United States Patent [19]

Friemel et al.

[11] Patent Number: 5,709,209
[45] Date of Patent: Jan. 20, 1998

[54] ULTRASOUND SIGNAL PROCESSING SYSTEM

[75] Inventors: Barry Friemel, Issaquah; John Klepper, Seattle, both of Wash.; Wolf DeLong, Erlangen, Germany; Rodney Boleyn, East Windsor, N.J.; Ekkehard Blanz, Belle Mead, N.J.; Abdelaziz Chihoub, Plainsborough, N.J.

[73] Assignee: Siemens Medical Systems, Inc., Iselin, N.J.

[21] Appl. No.: 729,057

[22] Filed: Oct. 10, 1996

Related U.S. Application Data

[63] Continuation-in-part of Ser. No. 625,183, Mar. 29, 1996, abandoned.

[51] Int. Cl.6 .................................................. A61B 8/00
[52] U.S. Cl. ........................................................ 128/660.07
[58] Field of Search ..................... 128/660.04, 660.07, 128/660.08, 660.09, 660.1, 661.01, 916; 73/620, 621, 625, 626

[56] References Cited

U.S. PATENT DOCUMENTS

| | | | |
|---|---|---|---|
| 5,492,125 | 2/1996 | Kim et al. | 128/660.07 |
| 5,535,748 | 7/1996 | Byrne et al. | 128/660.07 |
| 5,540,228 | 7/1996 | Li | 128/660.07 |

*Primary Examiner*—George Manuel

[57] ABSTRACT

An ultrasound medical imaging system having a flexible, versatile and programmable architecture, particularly with respect to a back end subsystem. The architecture for the back end subsystem is generalized and includes multiple identical and interchangeable processing elements or boards that combine to produce sufficient processing power to support real time imaging in the various modes of ultrasound operations. The architecture may also tune front end parameters for a front end subsystem based on back end processing, bypass faulty processing elements or boards, and/or distribute processing load across operational processing elements or boards. A method for operating such an ultrasound medical imaging system is also disclosed.

35 Claims, 9 Drawing Sheets

ULTRASOUND SIGNAL PROCESSING SYSTEM

CROSS-REFERENCE TO RELATED APPLICATIONS

This application is a continuation-in-part of U.S. patent application Ser. No. 08/625,183, filed 29 Mar. 1996.

BACKGROUND OF THE INVENTION

1. Field of the Invention

The present invention relates to an ultrasound system and, more particularly, to an ultrasound system having a flexible and high performance architecture.

Medical imaging systems are used as diagnostic tools for viewing internal areas of a patient's body. Imaging systems based on ultrasound technology are desirable because such systems are non-invasive, portable and generally easy to use.

Using medical ultrasound imaging systems, anatomical structures within a body of a patient can be displayed and analyzed. An ultrasound imaging system transmits sound waves of very high frequency (typically 2 MHZ to 10 MHZ) into the patient and then processes the echoes reflected from structures in the patient's body being examined. The purpose of the ultrasound imaging system is to display and/or analyze the return echoes. There are many types of displays used by ultrasound imaging systems, but probably the one most generally used is a two-dimensional image of a selected cross-section of the anatomical structure being examined. This mode of operation is called the echo mode (also known as B mode). Using the echo mode of operation, a number of anatomical defects in a patient can be detected. Furthermore, the size of these defects can be more or less precisely determined. In the echo mode of operation, all echoes from a selected cross-section are processed and displayed. The most critical operational parameter with respect to performance in this mode of operation is the size of the resolution cell. The size of the resolution cell can be decreased (thereby increasing resolution) by implementation of dynamic focusing and dynamic (matched) filtering.

In some clinical applications, anatomical defects can be relatively small and overshadowed by larger echoes. However, a small anatomical defect in or near a blood vessel may manifest itself by causing a relatively large change in the velocity of blood flowing in the vessel. It is known that a Doppler shift echo processing technique (known as Doppler mode) can be used for determining the velocity of a moving object. The display of Doppler shift for blood flow allows relatively small anatomical abnormalities to be more easily detected. In order to get more precise Doppler information about blood flow velocity from a small cross-section area, a Doppler processing technique such as described in an article by Halberg and Thiele published in the Hewlett-Packard Journal, pp. 35–40, June 1986, may be used. Using this technique it is possible to devote more time to a selected small area. The Doppler data is usually processed by Fast Fourier Transform (FFT) techniques and displayed by means of a spectrum.

Another mode of operation, known as color flow, allows information about blood velocity to be gathered from large selected cross-sections of the anatomical structure. Doppler color flow imaging displays blood flow as either red or blue depending on the direction of flow. Direction (towards or away from the transducer) is typically encoded with hue (red or blue), and velocity is encoded in brightness. The color flow mode is described in detail in U.S. Pat. No. 4,800,891.

It is difficult, however, to acquire sufficient ultrasound data to develop an accurate high resolution blood flow image at a sufficiently high frame rate.

To produce enough images per second to support real time imaging of a patient, ultrasound systems conventionally require separate processing boards for each processing task. A given processing board is designed to do specific tasks and typically is redesigned if processing requirements or processing algorithms change. An ultrasound system is thus conventionally constructed using dedicated hardware subsystems for each of many specific tasks.

The medical and ultrasound research community continue to improve ultrasound systems. However, the redesign of ultrasound systems is cumbersome and slow because of the complexity of the numerous special purpose processing boards within ultrasound systems. Ultrasound systems are also normally designed and built for dedicated clinical applications. As a result, ultrasound systems are not flexible enough to support varying clinical applications.

Hence, a significant problem with conventional ultrasound system architectures is that they lack flexibility, versatility and programmability. One recent attempt to provide a programmable platform for various clinical ultrasound applications is disclosed in U.S. Pat. No. 5,492,125. The programmable platform described therein, however, has limitations which restricts its flexibility, versatility and performance. One limitation is that the processing boards, although programmable, operate in a serial pipeline fashion. The serial pipeline design renders the ultrasound system susceptible to a high risk of failure should any one of the processing boards fail. Another limitation is that the transport of data between the processing boards is neither flexible nor of high bandwidth.

Thus, there is a need for an improved architecture for an ultrasound system that is flexible, versatile and programmable, yet still has sufficient processing power to support real time imaging.

SUMMARY OF THE INVENTION

The invention relates to an ultrasound system having a flexible, versatile and programmable architecture, particularly with respect to a back end subsystem. The architecture for the back end subsystem is generalized and includes multiple identical and interchangeable processing elements or boards that combine to produce sufficient processing power to support real time imaging in the various modes of ultrasound operations. The architecture may also tune front end parameters based on back end processing, bypass faulty processing elements or boards, and/or distribute processing load across operational processing elements or boards. The invention can be implemented in numerous ways, including as a system or a method. Several implementations are detailed below.

As an ultrasound imaging system, an embodiment of the invention includes: a transducer for sending acoustical signals towards a subject, the acoustical signals being formed in accordance with electrical scan signals; a front end subsystem for producing the electrical scan signals based on scan parameters, for receiving echo signals from the subject in response to the acoustical signals, and for producing vector signals from the echo signals; a back end processing subsystem for receiving the vector signals from said front end subsystem and processing the vector signals to produce image data and parameter information; a feedback link for feeding back the parameter information from said back end processing subsystem to said front end processing subsystem; and a display device for displaying an image in accordance with the image data.

Preferably, the feedback of the parameter information is performed in near real-time by said feedback link, and the parameter information being fed back via said feedback link causes the scan parameters used by said front end subsystem to be modified to improve the image to be displayed. It is also preferable that said back end processing subsystem include a plurality of substantially identical processing nodes and that a computation load associated with said back end processing system be distributed across said processing nodes. Furthermore, said ultrasound imaging system may include a controller for controlling said ultrasound imaging system. The controller determines said processing nodes within said back end processing subsystem that have failed and then bypasses said processing nodes that have failed so that the performance of said back end processing subsystem degrades gradually with the failure of each of said processing nodes.

As an ultrasound imaging system, an embodiment of the invention includes: a transducer for sending acoustical signals towards a subject, the acoustical signals being formed in accordance with electrical scan signals; a front end subsystem for producing the electrical scan signals based on scan parameters, for receiving echo signals from the subject in response to the acoustical signals, and for producing vector signals from the echo signals; a back end processing subsystem for receiving the vector signals from said front end subsystem and processing the vector signals to produce image data and parameter information, said back end processing subsystem includes at least a plurality of programmable processing nodes; a controller for controlling said ultrasound imaging system, the controlling including determining said processing nodes within said back end processing subsystem that have failed and then bypassing said processing nodes that have failed; and a display device for displaying an image in accordance with the image data.

As an ultrasound imaging system, an embodiment of the invention includes: a transducer for sending acoustical signals towards a subject, the acoustical signals being formed in accordance with electrical scan signals; a front end subsystem for producing the electrical scan signals based on scan parameters, for receiving echo signals from the subject in response to the acoustical signals, and for producing vector signals from the echo signals; a back end processing subsystem for receiving the vector signals from said front end subsystem and processing the vector signals to produce image data and parameter information, said back end processing subsystem includes at least a plurality of programmable processing nodes; a controller for controlling said ultrasound imaging system, the controlling including determining a computational load associated with said back end processing subsystem and then distributing the computational load to said programmable processing nodes; and a display device for displaying an image in accordance with the image data. Preferably, before distributing the computational load to said programmable processing nodes, the controlling by said controller determines said programmable processing nodes that are faulty and then bypasses said faulty programmable processing nodes.

As a method for operating an ultrasound imaging system, an embodiment of the invention includes the operations of: sending acoustical signals towards a subject, the acoustical signals being formed in accordance with electrical scan signals; producing the electrical scan signals based on scan parameters and for receiving echo signals from the subject in response to the acoustical signals; producing vector signals from the echo signals; processing the vector signals to produce image data and parameter information; tuning the scan parameters in real time in accordance with the parameter information; and displaying an image in accordance with the image data.

As a method for operating an ultrasound imaging system having a plurality of processing nodes for processing scan data, an embodiment of the invention includes the operations of: sending acoustical signals towards a subject, the acoustical signals being formed in accordance with electrical scan signals; producing the electrical scan signals based on scan parameters and for receiving echo signals from the subject in response to the acoustical signals; processing the echo signals into vector signals; determining a computational load for processing the vector signals; distributing the vector signals to the processing nodes for processing; processing the vector signals at the respective processing nodes to produce image data; and displaying an image in accordance with the image data.

There are numerous advantages associated with the ultrasound system and method according to the invention. One major advantage is that the back end processing subsystem no longer uses individually designed special purpose printed circuit boards. Instead, the ultrasound system utilizes substantially identical processing elements which are programmed to perform the back end processing operations. As a result, the failure of a small percentage of the processing elements does not cause the ultrasound system to fail as these processing elements can be bypassed, and if necessary, the available back end processing can be reduced so that the system gracefully degrades when processing elements fail. Another advantage of the ultrasound system is that the processing elements which are operational are not wasted in any given mode of the ultrasound system. For example, conventionally, the back end processing subsystem included separate boards for different back end processing paths associated with the different ultrasound modes. Hence, the failure of one such special purpose board caused the entire ultrasound system to fail to provide the particular ultrasound mode associated with the failed special purpose board. The particular ultrasound mode was thus unavailable until the failed special purpose board was repaired or replaced. However, according to the invention, the failure of certain of the processing elements does not affect the ability of the ultrasound system to provide all the features and modes normally provided. Further, regardless of the ultrasound mode, each of the processing elements is available to perform computations. The result is that the available processing power of the ultrasound system can be more effectively utilized. Yet another advantage of the invention is that the processing elements are generalized, programmable and interchangeable, such that hardware changes are not necessary when implementing design changes to the operation of the back end processing subsystem. Hence, design changes can be made in software without any hardware changes, thus resulting in reduced design time.

Other aspects and advantages of the invention will become apparent from the following detailed description, taken in conjunction with the accompanying drawings, illustrating by way of example the principles of the invention.

BRIEF DESCRIPTION OF THE DRAWINGS

The present invention will be readily understood by the following detailed description in conjunction with the accompanying drawings, wherein like reference numerals designate like structural elements, and in which.

DETAILED DESCRIPTION OF THE INVENTION

Ultrasound systems must support various modes of operation in an efficient and flexible manner. An ultrasound system according to the invention includes an improved architecture that is flexible, versatile and programmable, particularly with respect to back end processing for the various modes of operation. The architecture for the back end subsystem is generalized and includes multiple identical and interchangeable processing elements or boards that combine to produce sufficient processing power to support real time imaging in the various modes of ultrasound operation. The architecture may also tune front end parameters based on back end processing, bypass faulty processing elements or boards, and/or distribute processing load across operational processing elements or boards.

Embodiments of the invention are discussed below with reference to FIGS. 1–9. However, those skilled in the art will readily appreciate that the detailed description given herein with respect to these figures is for explanatory purposes as the invention extends beyond these limited embodiments.

Figure 1:
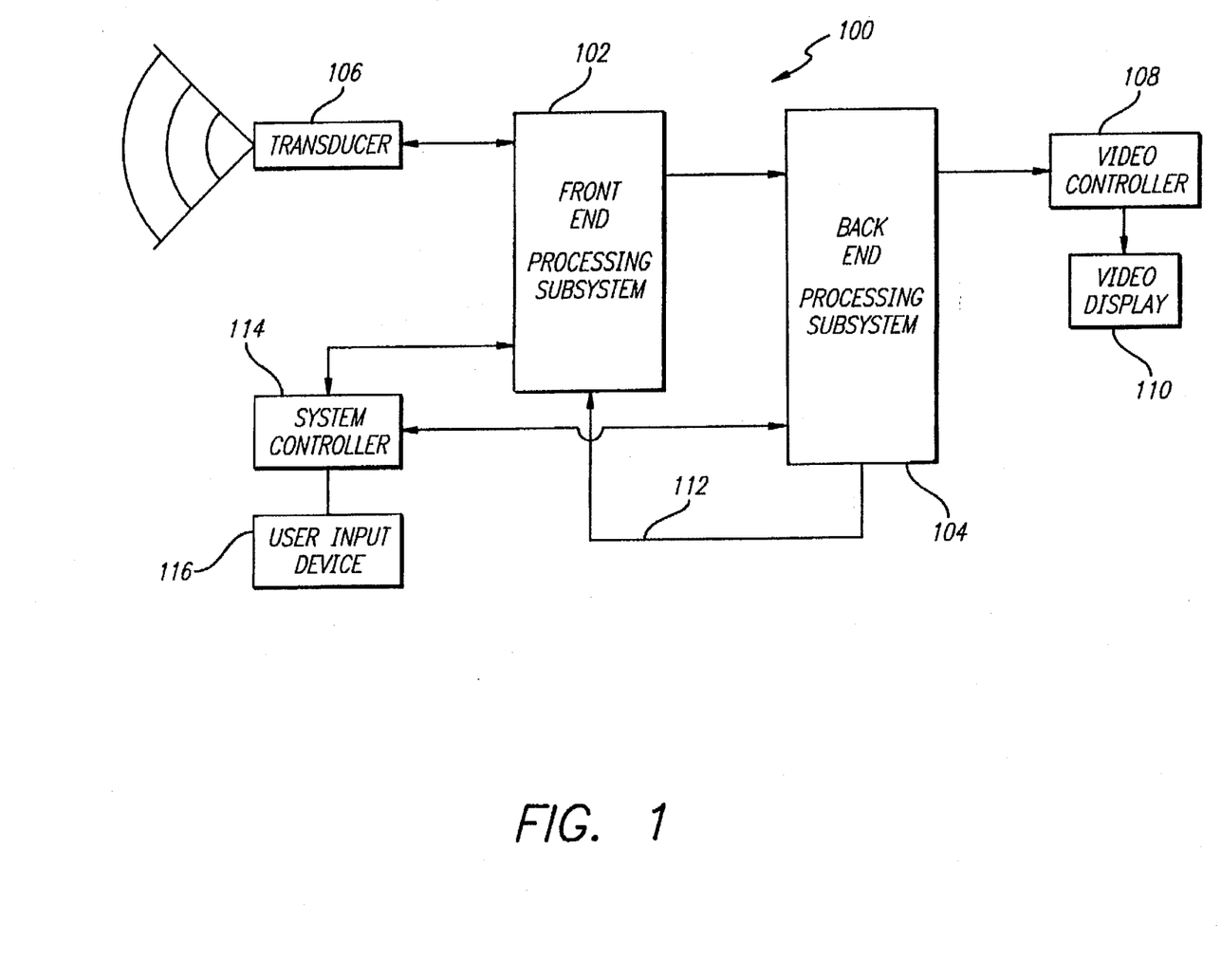
FIG. 1 is an ultrasound system for producing ultrasound images according to an embodiment of the invention.

FIG. 1 is an ultrasound system 100 for producing ultrasound images according to an embodiment of the invention. The ultrasound system 100 includes a front end processing subsystem 102 and a back end processing system 104. The front end processing subsystem 102 is coupled to a transducer 106. The transducer 106 operates to generate and receive acoustic signals. The acoustic signals that are generated by the transducer 106 are directed towards a body region of a patient, and then reflected back to the transducer 106 as echo signals. The echo signals obtained by the transducer 106 are then forwarded to the front end processing subsystem 102.

After some front end processing of the echo signals within the front end processing subsystem 102, vector data associated with the echo signals are produced by the front end processing and then supplied to the back end processing subsystem 104. The elements in these vectors represent the value of some parameter or parameters related to the spatial location of the received echo signals. Examples of these parameters are the magnitude of the echoes, the harmonic content of the echoes, or any other parameters that may be derived directly from the combination of signals from multiple elements in the transducer array or repetitive transmission and reception of acoustic signals from the array.

As such, each vector consists of a series of numbers in a multidimensional space. A plurality of vectors which may include multiple beams or beam segments formed from one or more transmissions may be passed together to the back-end processor. each vector dimension may contain one or more components including, but not limited to, complex data, spatial coordinates or multiple members of an ensemble.

The back end processing subsystem 104 performs back end processing which includes, for example, echo signal processing, color flow processing, and Doppler processing. The echo signal processing is performed when the ultrasound system 100 is in the echo mode, the color flow processing is performed when the ultrasound system 100 is in the color flow mode, and the Doppler processing is performed when the ultrasound system 100 is in the Doppler mode. The end result of the back end processing is raster data that is used to display the ultrasound image. The raster data output from the back end processing subsystem 104 is then supplied to a video controller 108. The video controller 108 controls a video display 110 whereon the ultrasound image is displayed. The back end processing performed by the back end processing subsystem 104 also determines and feeds back parameter adjustment information to the front end processing subsystem 102 via a feedback bus 112. The feedback bus 112 is, more generally, a link. The feedback bus 112 provides a high speed connection between the back end processing subsystem 104 and the front end processing subsystem 102. The back end processing subsystem 104 and its interaction with the feedback bus 112 are discussed in detail below.

The ultrasound system 100 also includes a system controller 114 and a user input device 116. The system controller 114 operates to initiate and to perform overall control of the ultrasound system 100. In controlling the ultrasound system 100, the system controller 114 sends and receives control signals to and from both the front end processing subsystem 102 and the back end processing subsystem 104. Examples of the specific control operations performed by the system controller 114 include, for example, the scheduling of very high level tasks. The user input device 116 is coupled to the system controller 114 for supplying user input thereto. The user input device 116 can, for example, be a keyboard, a pointing device, knobs, dials, and the like.

Figure 2:
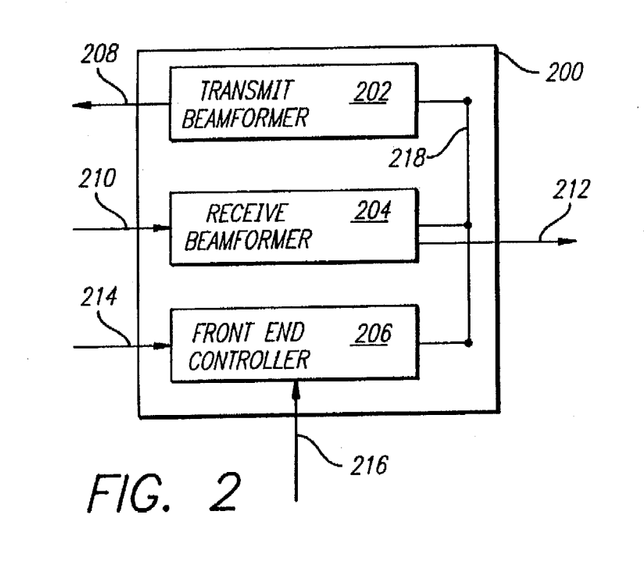
FIG. 2 is a block diagram of a front end processing subsystem according to an embodiment of the invention.

FIG. 2 is a block diagram of a front end processing subsystem 200 according to an embodiment of the invention. The front end processing subsystem 200 is a more detailed embodiment of the front end processing subsystem 102 illustrated in FIG. 1. The front end processing subsystem 200 includes a transmit beam former 202, a receive beamformer 204, and a front end controller 206. The transmit beamformer 202 produces driving signals 208 for the transducer 106. The receive beamformer 204 receives echo signals 210 from the transducer 106 and produces vector signals from the echo signals 210. The transmit beamformer 202 and the receive beamformer 204 support one or more beams. The front end controller 206 controls the transmit beamformer 202 and the receive beamformer 204. The front end controller 206 receives control signals 214 from the system controller 114 and receives feedback information 216 from the back end processing subsystem 104. The front end controller 206, the receive beamformer 204, and the transmit beamformer 202 are electrically coupled, preferably by a bus 218, so that data and control signals can be passed between these devices. One of the major functions of the front end controller 206 is to provide the transmit beamformer 202 and the receive beamformer 204 with image parameters to guide their operation. The feedback information 216 from the back end processing subsystem 104 (via feedback bus 112) is used by the front end controller 206 to modify the image parameters based on processing performed by the back end processing subsystem 104 as will be explained in detail below.

The objective of beamforming in a system is to form a narrow beam for improving reception of an echo signal arriving from a desired location with respect to a patient's body in the presence of noise and interfering signals from other locations. Beamforming can be performed during energy transmission or reception. Accordingly, the front end processing subsystem 200 includes the transmit beamformer 202 and the receive beam former 204. Further, the size of the resolution cell can be decreased (thereby increasing resolution) by implementation of dynamic focusing and dynamic (matched) filtering. These techniques are easier to implement with a digital beamformer than with an analog beamformer. A suitable digital beamformer is described in U.S. Pat. No. 5,369,624.

The quality of the beamforming influences the accuracy, resolution and other parameters of the echo (B), Doppler or color flow modes of operation of the ultrasound system 100. A conventional beamformer electronically provides time delays to match the signal propagation delays of the ultrasound pressure field which is incident upon the ultrasound beamformer from a specific direction. This time-delay (or spatial processing) enhances the amplitude of the coherent wavefront relative to the background noise and directional interference. In an analog beamformer, this is done using analog delay lines and summing networks. These analog components restrict modem ultrasound diagnostic equipment in many different ways (and are therefore undesirable). The increase of performance and reliability and decrease of cost of digital components makes digital beamforming a more promising alternative as compared to classical analog beamforming. Precision, stability and flexibility are the main advantages of digital signal processing techniques. The current standard digital circuitry can work at Nyquist rates exceeding 30 MHZ. These sampling frequencies are high enough for RF sampling and temporal processing of modem ultrasound signals. However, the sampling rate required to properly match the propagation delays in a digital beamformer is several times greater than the Nyquist rate for accurate signal reconstructions (i.e., greater than 100 MHZ. These processing speeds, coupled with the required processing are still above the performance levels of presently available analog-to-digital converters (ADCs). The remaining digital functions (e.g. other than the ADC's) can be performed at these speeds by parallel processing using standard digital components.

Figure 3:
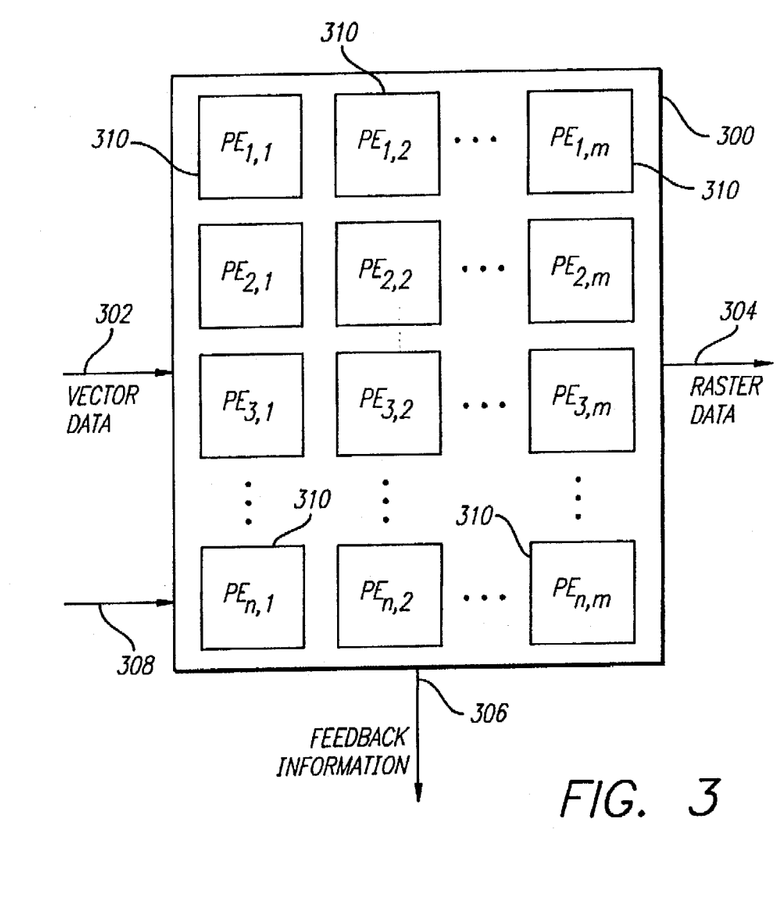
FIG. 3 is a block diagram of a back end processing subsystem according to a first embodiment of the invention.

FIG. 3 is a block diagram of a back end processing subsystem 300 according to a first embodiment of the invention. The back end processing subsystem 300 is an exemplary embodiment of the back end processing subsystem 104 of FIG. 1. The back end processing subsystem 300 receives vector data 302 from the front end processing subsystem 102 and outputs raster data 304 to the video controller 108 which in turn causes an image to be displayed on the video display 110.

The back end processing performed by the back end processing system 300 which includes, for example, echo signal processing, color flow processing, and Doppler processing. The back end processing may also include scan conversion processing, image processing and video processing. In addition, the back end processing subsystem 300 produces feedback information 306 which is forwarded directly to the front end processing subsystem 102, 200. Control signals 308 from the system controller 114 are also received by the back end processing subsystem 300.

The echo signal processing typically encompasses signal enhancement filtering, energy detection and image enhancement filtering. Various known filtering and convolution techniques are employed. The basic purpose of echo signal processing is to enhance the signal to noise ratio of the echo signal.

Flow signal processing analyzes signals for flow parameters. Typical parameter derivations include sample correlation and flow averaging. The purpose of flow signal processing is to identify flow and turbulence within a scanned area.

Doppler signal processing typically encompasses signal enhancement filtering, spectral estimation processing, energy detection, and derived waveform filtering. The purpose of Doppler signal processing is to identify and filter out Doppler shift, to improve spectral frequency response, and to coordinate spectral mapping.

Scan conversion processing converts the processed vector data streams from echo signal processing and flow signal processing. When the transducer 106 performs sector scanning, the vector signals are digital polar-coordinate data samples of echo, flow and/or Doppler signals. When the transducer 106 performs linear scanning, the vector signals are digital Cartesian-coordinate data samples of echo, flow and/or Doppler signals. For polar-coordinate vector data, the data is converted by the scan conversion processing into Cartesian-coordinate raster data. For Cartesian-coordinate vector data the data is scaled by the scan conversion processing into Cartesian-coordinate raster data.

Image processing includes image enhancement processes executed on the raster data or vector data. In an off-line delayed playback mode of operation image data, vector data and/or raster data is received from an image memory and processed. Image processing tasks for varying applications include, for example, histogram equalization, contrast limited adaptive histogram equalization, edge enhancement, boundary enhancement, 2-D graphics, 3-D volume visualization, tissue characterization, perfusion measurements, image segmentation, edge detection and speckle reduction.

Video processing executes on the image processed data to generate video signals, audio signals, and graphing signals for output to a display device, audio device, storage device (e.g., VCR) and/or charting device. Video processing in some applications also executes on Doppler processed vector data to generate similar video signals, audio signals, and graphing signals for output to the display device, audio device, storage device and/or charting device.

According to the invention, image processing, echo signal processing, flow signal processing, Doppler signal processing, scan conversion and/or video processing are hosted on the back end processing subsystem 300. To carry out the back end processing, the back end processing subsystem 300 includes a plurality of processing elements 310. The processing elements 310 illustrated in FIG. 3 are arranged in a two-dimensional array with each row having m processing elements and each column having n processing elements. Thus, in the embodiment of the back end processing subsystem 300 illustrated in FIG. 3, there are m×n processing elements. Each of the processing elements 310 are substantially identical and reprogrammable. Hence, each of the processing elements 310 is just as capable as processing vector data as any other processing element 310. Each of the processing elements is also capable of altering its programming or processing dynamically during imaging. Buses, although not shown in FIG. 3, interconnect the processing elements 310. Preferably, the buses not only interconnect the processing elements 310, but also supply the vector data 302 to each of the processing elements 310, obtain raster data from each of the processing elements 310, supply control signal 308 to each of the processing elements 310, and forward feedback information 306 from each of the processing elements 310 to the front end processing subsystem 102.

Figure 4A:
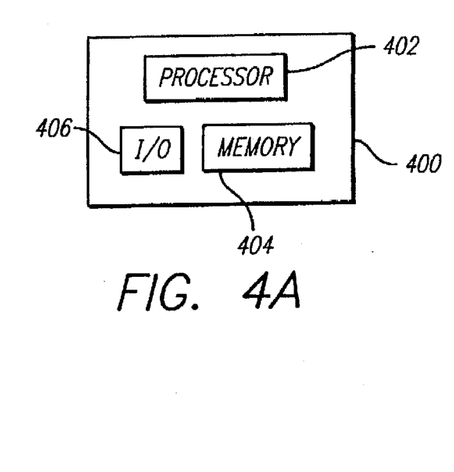
FIG. 4A is a block diagram of a processing element in accordance with an embodiment of the invention.
Figure 4B:
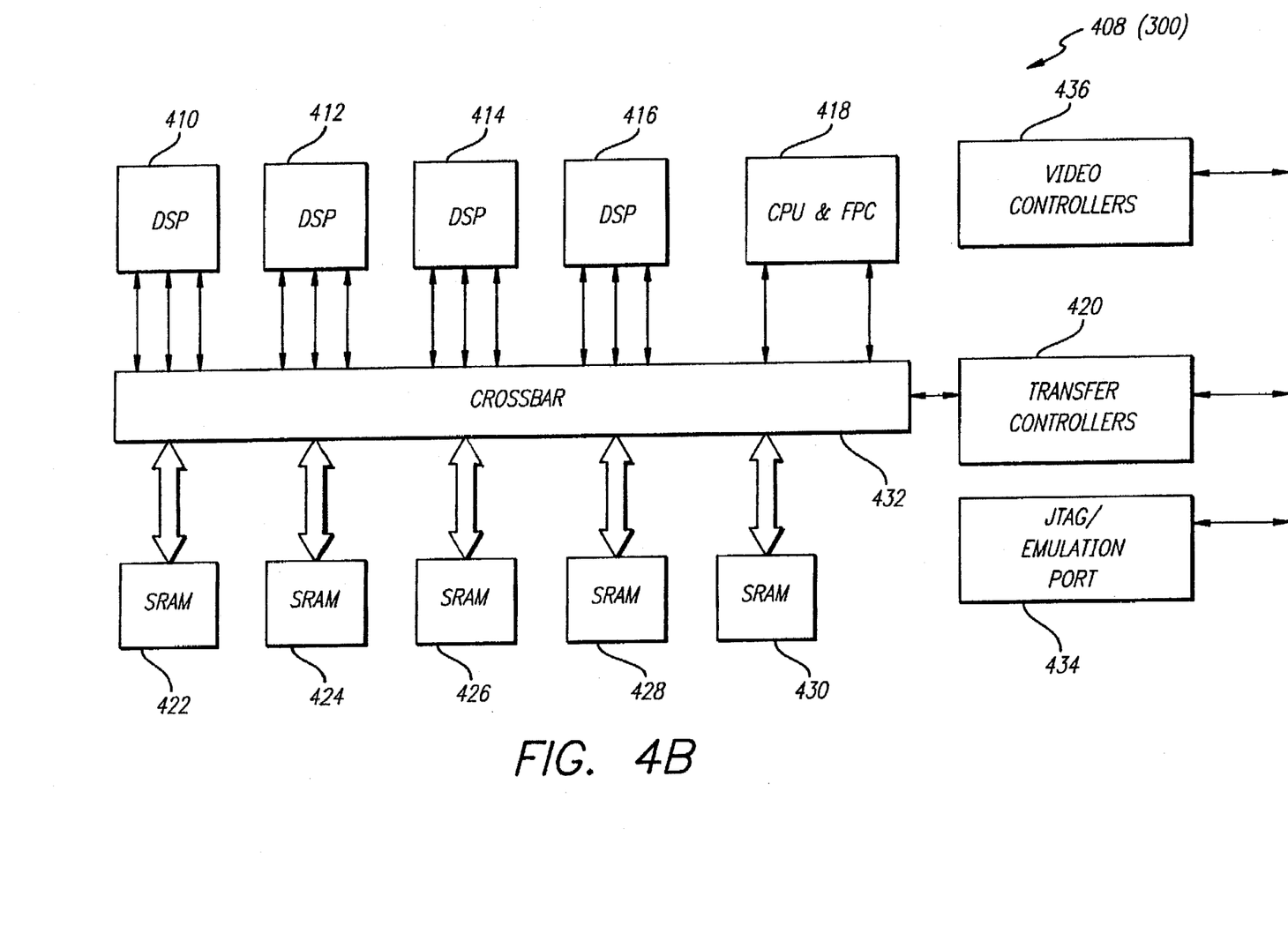
FIG. 4B is a detailed block diagram of a processing element in accordance with another embodiment of the invention.

FIG. 4A is a block diagram of a processing element 400 in accordance with an embodiment of the invention. The processing element 400 is an exemplary embodiment of the processing element 310 of FIG. 3. The processing element 400 includes a processor 402, a memory 404, and an input/output (I/O) manager 406. Hence, the processing element 400 can be any of many commercially available microprocessors, special purpose processors, ASIC processors or reprogrammable FPGAs. In FIG. 4B, an example of a special purpose processor known as a multiprocessor is illustrated.

FIG. 4B is a detailed block diagram of a processing element 408 in accordance with another embodiment of the invention. The processing element 408 is an exemplary embodiment of the processing element 310 of FIG. 3. The processing element 408 includes one or more digital signal processors. As an example, the processing element 408 could be a multiprocessor such as a Texas Instruments multimedia video processor ("MVP") (part no. TMS320C80). The processing element 408 combines on a single semiconductor chip, four fully programmable digital signal processors 410, 412, 414, 416 and a master processor 418 for handling multiple data streams via a transfer controller 420. Several on-chip random access memory (RAM) devices 422, 424, 426, 428, 430 serve as resident memory accessible to the digital signal processors (DSPs) 410–416 via a crossbar network 432. Each digital signal processor (DSP) 410–416 includes two address generators, three input 32-bit ALUs, a 16×16 multiplier, three zero overhead loop controllers, and a 32-bit barrel shifter. Each RAM 422–430 has a 10 kB capacity providing 50 kB of single-cycle SRAM. Memory 422–430 is partitioned in blocks with each block serving as either data RAM, parameter RAM, data cache or instruction cache. The data caches and instruction caches serve as a primary cache. The transfer controller 420 services the on-chip caches and interfaces to external memory. The Texas Instruments MVP has a throughput rating of approximately 2 billion operations per second. The master processor 418 is a RISC processor with an integral floating point unit. According to this embodiment of the processing element 408, the master processor 418 coordinates and distributes processing tasks among the DSPs 410–416 and manages external off-chip communications. A JTAG/emulation port 434 is included for use in testing, development and diagnostics. The processing element 408 also includes a pair of video controllers 436. The video controllers 436 are useful to generate video synchronization signals or to synchronize data transfer rates with external video signals.

Figure 5:
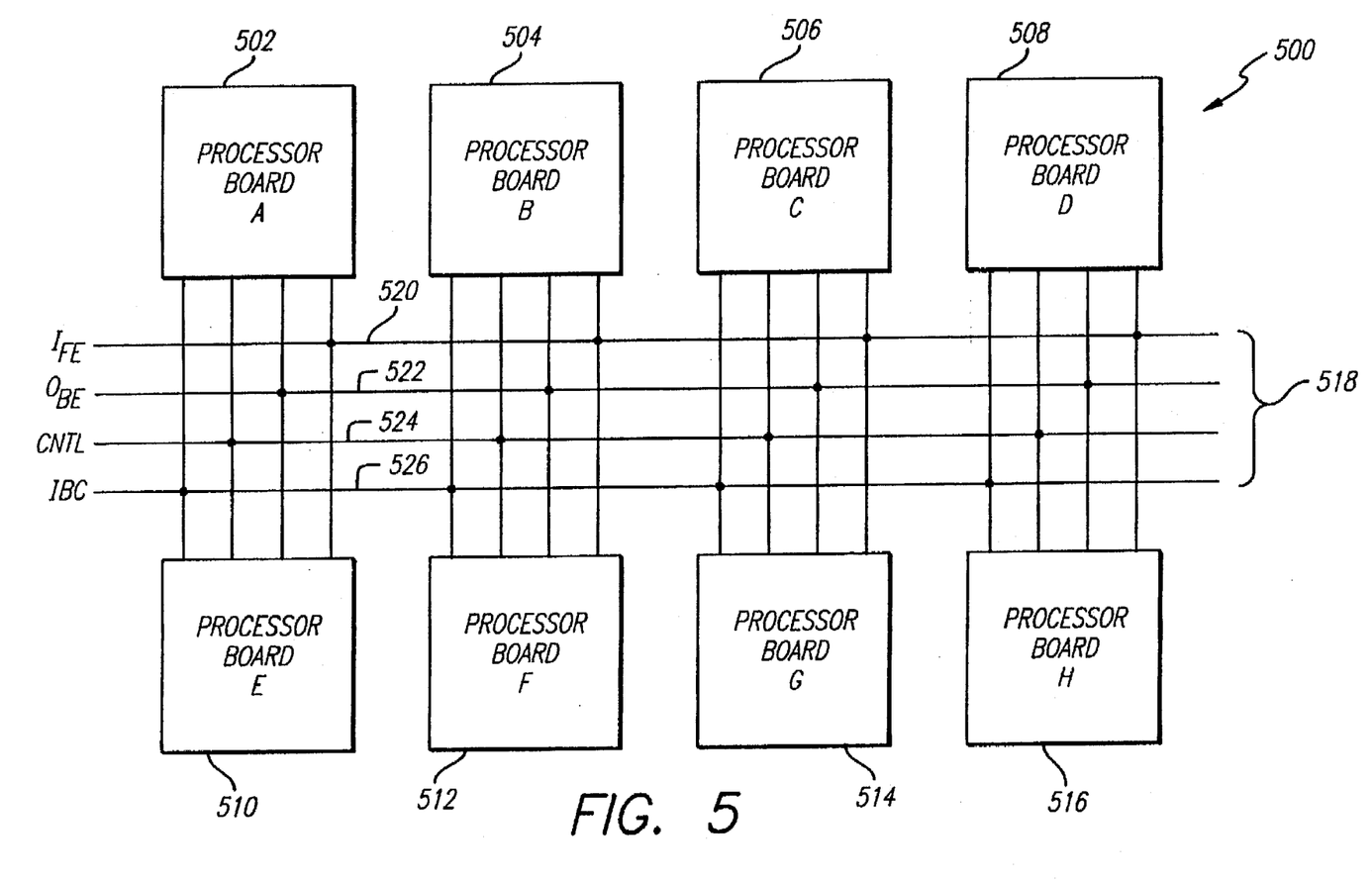
FIG. 5 is a back end processing subsystem according to a second embodiment of the invention.

FIG. 5 is a back end processing subsystem 500 according to a second embodiment of the invention. The back end processing subsystem 500 is an exemplary embodiment of the back end processing subsystem 104 of FIG. 1. The back end processing subsystem 500 includes multiple substantially identical processor boards. Specifically, the back end processing subsystem 500 includes a processor board A 502, a processor board B 504, a processor board C 506, a processor board D 508, a processor board E 510, a processor board F 512, a processor board G 514, and a processor board H 516. The back end processing subsystem 500 also includes a plurality of buses 518, known as global backplane buses, which couple to the processor boards 502–516. These buses 518 include an input bus ($I_{FE}$) 520 which receives incoming signals from the front end processing subsystem 102. An output bus ($O_{BE}$) 522 is used to forward data from the processor boards 502–516 to the video controller 108. A control bus (CNTL) 524 receives and supplies parameter information to the front end processing subsystem 102. The control bus (CNTL) 524 incorporates or is coupled to the feedback bus 112 shown in FIG. 1 so that the parameter information (feedback information) can be directly coupled to the front end processing subsystem 102. An inter-board communication bus (IBC) 526 is used to transmit control and data signals between the processor boards 502–516 within the back end processing subsystem 500. Although it may be preferable to have four separate buses in the global backplane with distinct uses, it is not required that each bus have a distinct use or that the number of buses in the global backplane be a certain number.

Although the back end processing subsystem 500 illustrated in FIG. 5 includes eight (8) substantially identical processor boards, the number of processor boards required will vary depending on the computing power of the processor boards as well as the computing and responsiveness requirements of the ultrasound system. Fortunately, the architecture of the back end processing system is scalable for various levels of performance. For example, one processor board could be used in a low-medium price system, two or three processor boards could be used in a medium-high price system, and four processor boards could be used in a high price system. Hence, both performance and price scale with the number of processor boards in the system. In other words, by adding processor boards, the system increases its performance and the features it can provide.

Figure 6:
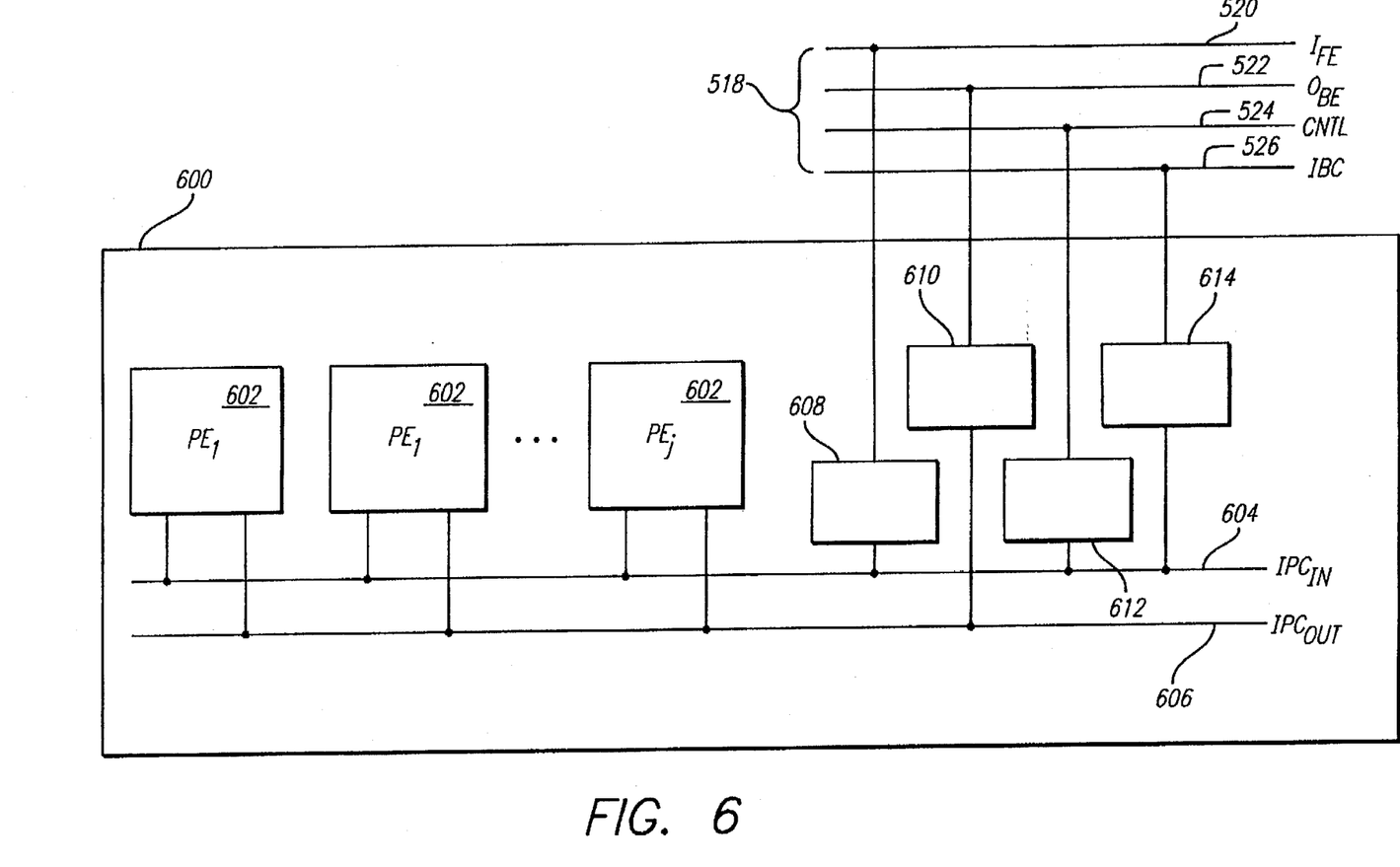
FIG. 6 is a block diagram of a processor board according to an embodiment of the invention.

FIG. 6 is a block diagram of a processor board 600 according to an embodiment of the invention. The processor board 600 is representative of the processor boards 502–516 illustrated in FIG. 5. The processor board 600 includes processing elements $PE_i$–$PE_j$ 602, an inter-processor communication input ($IPC_{IN}$) bus 604, and an inter-processor communication output ($IPC_{OUT}$) bus 606. The processing elements $PE_i$–$PE_j$ 602 can, for example, be similar to the processing elements 310, 400, 408 discussed above. The $IPC_{IN}$ bus 604 and the $IPC_{out}$ bus 606 are local buses residing on the processor board 600 and provide interconnection between the processing elements 602 (inter-processor communication). The $IPC_{IN}$ bus 604 and the $IPC_{OUT}$ bus 606 also provide interconnection to buses 518 of the global backplane. The processor board 600 includes a first bus interface device 608, which interfaces (couples) the $IPC_{IN}$ bus 604 to the input bus 520 ($I_{FE}$) 520 of the back end processing subsystem 500. A second bus interface device 610 interfaces (couples) the $IPC_{OUT}$ bus 606 with the output bus ($O_{BE}$) 522 of the back end processing subsystem 500. A third bus interface device 612 interfaces (couples) the $IPC_{IN}$ bus 604 with the control bus (CNTL) 524 of the back end processing subsystem 500. A fourth bus interface device 614 interfaces the $IPC_{IN}$ bus 604 with the IBC bus 526 of the back end processing subsystem 500. Although the embodiment of the processor board 600 illustrated in FIG. 6 includes separate input and output IPC buses 604 and 606, it should be understood that only one bus is required on the processor board 600 and that more than two buses could also be utilized, depending upon the particular application and the amount of data that must be passed between the processing elements 602. The processor board 600 can also be considered another exemplary embodiment of the processing element 310 of FIG. 3.

Figure 7A:
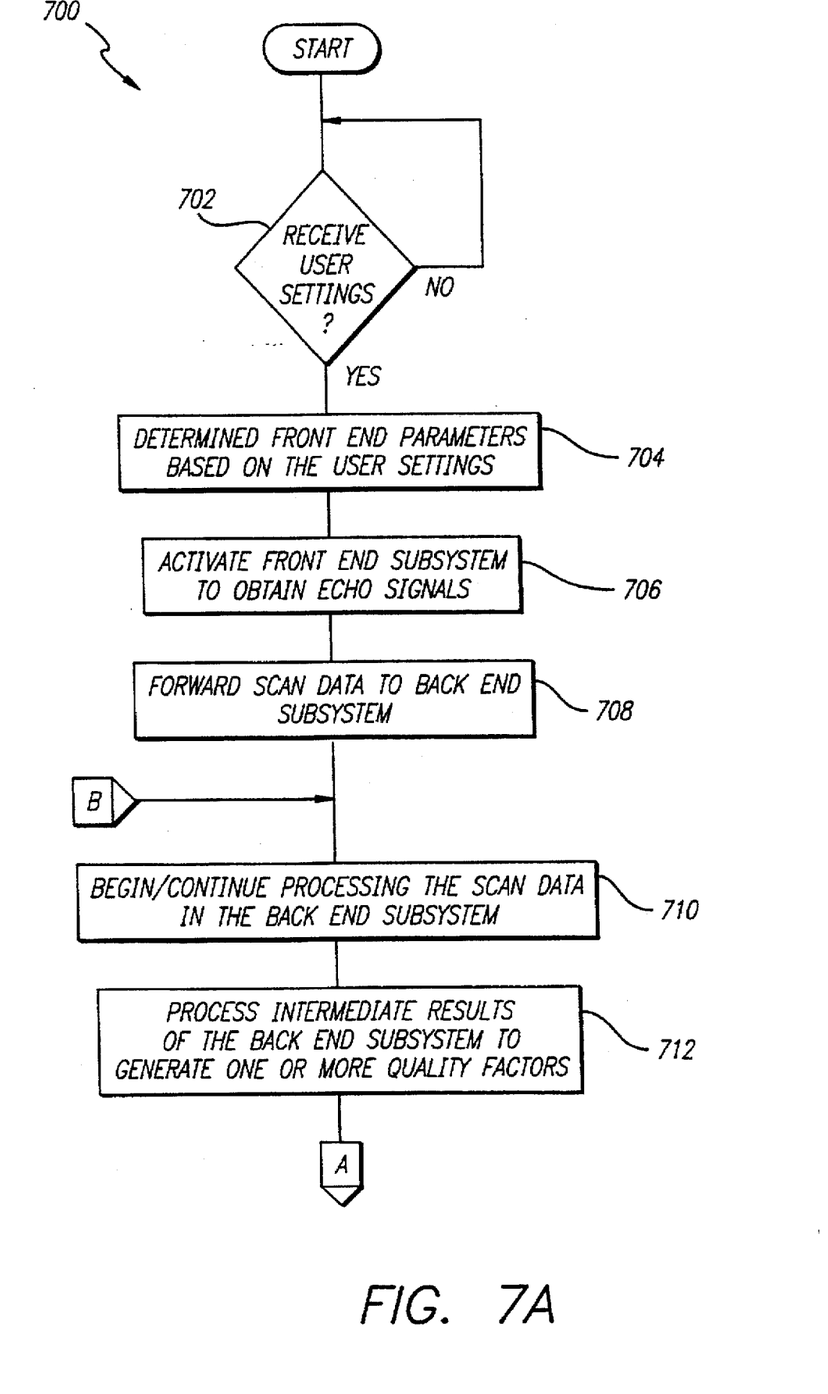
FIGS. 7A and 7B are flow diagrams of ultrasound processing according to an embodiment of the invention.
Figure 7B:
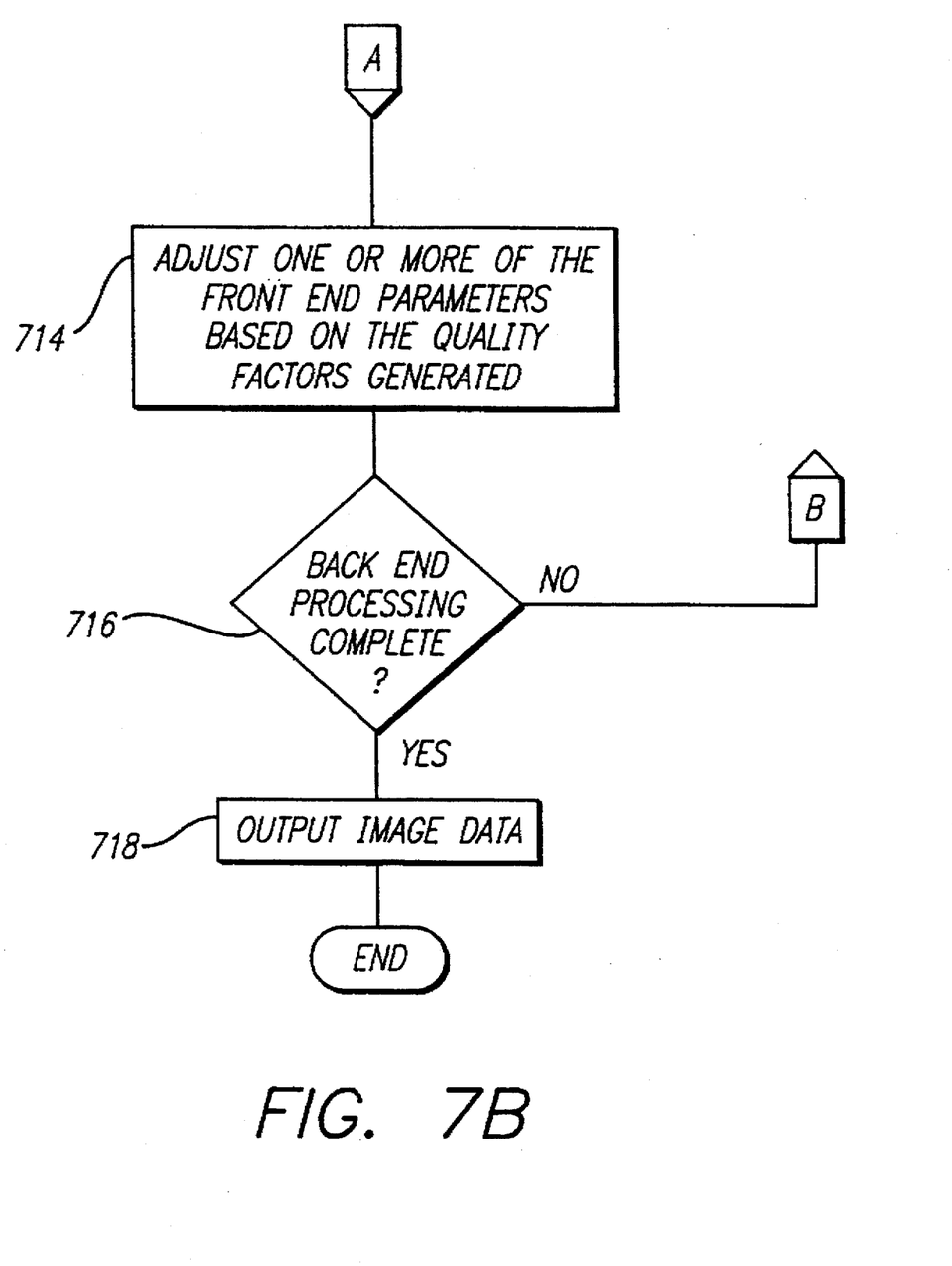

FIGS. 7A and 7B are flow diagrams of ultrasound processing 700 according to an embodiment of the invention. The ultrasound processing 700 is performed by the ultrasound system 100.

The ultrasound processing 700 begins with a decision 702 which determines whether user settings have been received. The user settings are set by a user using the user input device 116. If the user settings have not yet been input into the ultrasound system 100, the ultrasound processing 700 awaits their reception. Once the user settings have been received, the ultrasound processing 700 continues because the user is prepared to take an image using the ultrasound system 100. Following the decision block 702, front end parameters are determined 704 based on the user settings. The front end parameters are also referred to as image parameters and scan parameters. Here, the system controller 114 and/or the front end controller 206 operate to determine the appropriate front end parameters for the transmission and reception of acoustical signals by the front end processing subsystem 102. Next, the front end processing subsystem is activated 706 by the system controller 114 to obtain scan data for an image. That is, the front end processing subsystem 102, 200 activates the transducer 106 to obtain the desired echo signals from a subject patient. The echo signals are converted into vector data by some front end processing operations performed in the front end processing subsystem 102, 200. The vector data is also referred to as scan data. After the front end processing subsystem 102, 200 obtains the scan data, the scan data is forwarded 708 to the back end processing subsystem 104, 300, 500. The front end processing subsystem 102, 200 receives the echo signals and performs some initial processing on the echo signals to form the scan data. The scan data is then forwarded 708 to the back end processing subsystem 104, 300, 500.

Next, the scan data that has been received in the back end processing subsystem 104, 300, 500 begins to be processed 710 therein. During the processing of the scan data, intermediate results of the back end processing subsystem 104, 300, 500 are processed 712 to generate one or more quality factors. As an example, an intermediate result is a Doppler spectrum and an associated quality factor would be peak velocity. Then, one or more of the front end parameters are adjusted 714 based on the quality factors. An example of a front end parameter that would be adjusted is pulse repetition frequency.

Here, the back end processing subsystem 104, 300, 500 is producing feedback information while processing the scan data. Namely, the feedback information is the quality factors or the adjusted front end parameter. As intermediate results and quality factors are generated or produced, the front end parameters which are used to obtain the echo signals can be modified so as to produce an improved ultrasound image. Next, a decision 716 determines whether the back end processing is complete. If the back end processing is not yet completed, the processing 700 returns to repeat block 710 and subsequent blocks. Hence, it is preferred that the adjustment of the front end parameters occur while an initial set of the scan data for the image is being processed. Hence, the echo signals for scan data associated with later parts of the same image can be affected by the processing of the earlier parts of the image. Thus, as long as the back end processing is not yet completed, the feedback (e.g., via feedback bus 112, 524) of the feedback information to the front end processing subsystem 102, 200 can be utilized to affect the echo signals (and consequently the scan data) for latter portions of the image being scanned. The feedback information may be used to adjust the front parameters for the same image or a next image. When the image is processed in segments or portions as the invention allows, the feedback information can affect echo signals for later portions of the same image. This near real-time feedback is facilitated by the feedback bus 112, 524 which provides a direct, high-speed communication link to the front end processing subsystem 102, 200. On the other hand, once the back end processing is completed, a decision block 716 causes the image data to be output 718 to the video controller 108 and, in turn, to the video display 110. Following block 718, the ultrasound processing 700 is complete and ends.

The processing 710 of the scan data in the ultrasound processing 700 starts processing the scan data a block at a time. In other words, the substantially identical programmable processing elements of the back end processing subsystem 104, 300, 500 are preferably operated in a round-robin approach, where each processing element starts when it receives the data needed for its processing. Alternatively, all the processing elements could begin when all the scan data to be processed is distributed.

Figure 8:
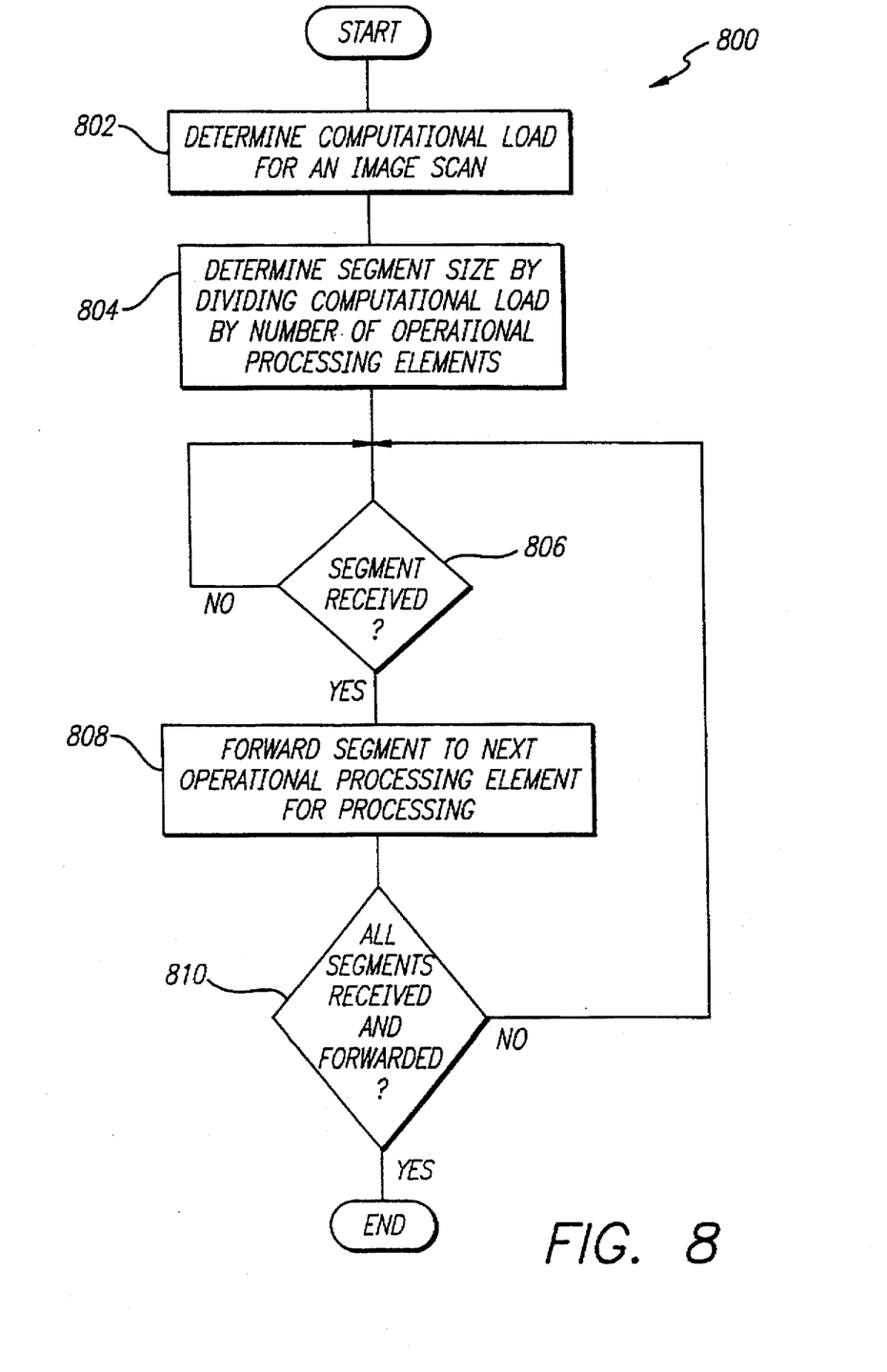
FIG. 8 is a flow diagram of image allocation processing according to an embodiment of the invention.

FIG. 8 is a flow diagram of image allocation processing 800 according to an embodiment of the invention. The image allocation processing 800 is preferably performed by the system controller 114 to allocate or distribute computational tasks associated with back end processing to the various programmable processing elements of the back end processing system 104, 300, 500.

The image allocation processing 800 initially determines 802 a computational load for an image scan. The computational load of interest is the computational load that must be performed in the back end processing system 104, 300, 500 for the image scan. Preferably, the computational load is determined by the system controller 114 based on the amount of vector data produced by the front end processing subsystem 102, 202. The amount of vector data is affected by front end parameters, processing mode, and other system configuration information. Namely, the computational load can be estimated by weighting the number of vectors in the vector data received for the particular mode of processing to be carried out.

Next, a segment size is determined 804 by dividing the computational load by the number of operational processing elements. The segment size relates to the mount of vector data for an image that are to be processed by an individual processing element. Alternatively, in a board level design such as illustrated in FIG. 5, the computational load could be divided by the number of processor boards. Following block 804, a decision block 806 determines whether a segment of data (vectors) has been received. If a segment has not been received, the processing 800 waits until a segment is received. Once a segment is received, the image allocation processing 800 forwards 808 the received segment to the next operational processing element for processing of the segment. Hence, if the segment received is the first segment, then the first segment is forwarded to the first operational processing element. The first operational processing element then carries out processing for the first segment, while at the same time other segments of the image are received. The bus arrangements illustrated in FIGS. 5 and 6 are preferred for such segmented processing. Next, a decision block 810 determines whether all segments of the image have been received and forwarded to respective processing elements. If all the segments have not been received and forwarded, the image allocation processing 800 returns to repeat blocks 806 and subsequent blocks. On the other hand, once all the segments have been received and forwarded, the image allocation processing 800 is complete and ends.

The image allocation processing 800 operates to balance the computational load for an image scan across the operational processing elements. In one embodiment, the segment size could be the number of data elements of the vector data for the scan image that are to be processed by a single one of the processing elements. The data elements may or may not be whole vectors. Ideally, each processor would get the same number of data elements to process. However, the amount of data elements or the amount of work to be processed may also not be distributed equally to each of the processing nodes because the processing nodes may not all be identical, and thus some processing nodes operate faster than others. Another reason that the segments sizes are not all equal is that not all the processing nodes operate on the same kind of data.

Figure 9:
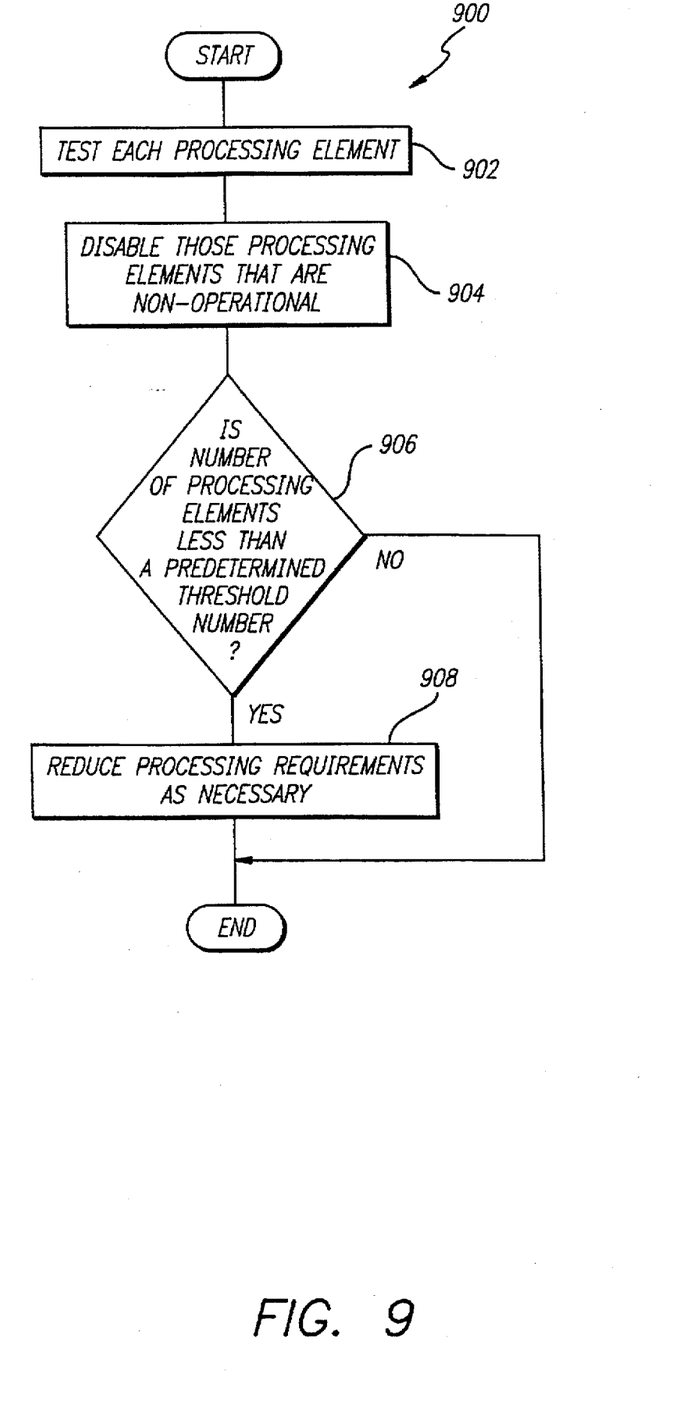
FIG. 9 is a flow diagram of processor test processing according to an embodiment of the invention.

FIG. 9 is a flow diagram of processor test processing 900 according to an embodiment of the invention. The processor test processing 900 together with the bus architecture discussed above allows the ultrasound system to avoid failed processing elements or boards while still appearing to the user to operate properly.

The processor test processing 900 tests 902 each of the processing elements. The test performed can be performed either by the processing element itself or by the system controller 114. Next, those processing elements that are determined by the testing to be non-operational are disabled 904. The faulty processing elements can be disabled from the buses by placing buffers between the processing elements and the buses and then isolating the faulty processing elements from the buses by placing the outputs of the buffers in a high impedance state. For example, the interface devices 608-614 illustrated in FIG. 6 could include such buffers to provide board level isolation. Alternatively, the processing elements could couple to the input and output IPC buses 604 and 606 via buffers (not shown) to provide the capability of individually isolating each of the processing elements. In either case, the faulty processing elements or processor boards are bypassed (i.e., not allocated any processing responsibilities). A decision 906 next determines whether the number of available processing elements is inadequate, i.e., less than a predetermined threshold number. If the number of available processing elements is less than the predetermined threshold number, then the processing requirements within the back end processing subsystem 104, 300, 500 are limited or reduced 908 as is necessary to operate correctly with a reasonable response time given the availability of the processing elements. On the other hand, if the number of available processing elements is not less than the predetermined threshold number, then it is determined that the back end processing subsystem 104, 300, 500 has sufficient processing power to complete the processing of the image scan with full usage of the features that are available. Following block 908, the processor test processing 900 is complete and ends.

There are numerous advantages associated with the ultrasound system and method according to the invention. One major advantage is that the back end processing subsystem no longer uses individually designed special purpose printed circuit boards. Instead, the ultrasound system utilizes substantially identical processing elements which are programmed to perform the back end processing operations. As a result, the failure of a small percentage of the processing elements does not cause the ultrasound system to fail as these processing elements can be bypassed, and if necessary, the available back end processing can be reduced so that the system gracefully degrades when processing elements fail. Another advantage of the ultrasound system is that the processing elements which are operational are not wasted in any given mode of the ultrasound system. For example, conventionally, the back end processing subsystem included separate boards for different back end processing paths associated with the different ultrasound modes. Hence, the failure of one such special purpose board caused the entire ultrasound system to fail to provide the particular ultrasound mode associated with the failed special purpose board. The particular ultrasound mode was thus unavailable until the failed special purpose board was repaired or replaced. However, according to the invention, the failure of certain of the processing elements does not affect the ability of the ultrasound system to provide all the features and modes normally provided. Further, regardless of the ultrasound mode, each of the processing elements is available to perform computations. The result is that the processing power of the ultrasound system can be more effectively utilized. Yet another advantage of the invention is that the processing elements are generalized, programmable and interchangeable, such that hardware changes are not necessary when implementing design changes to the operation of the back end processing subsystem. Hence, design changes can be made in software without any hardware changes, thus resulting in reduced design time.

Some of the scan parameters (front end parameters) used by the front end processing subsystem 102, 200 include parameters such as: a look direction (also known as steering), center frequency, transmit and receive focal points, pulse repetition frequency (PRF), apodization (time delay) coefficients, angle of interrogation, pulse length, and pulse shape, and ensemble lengths. The scan parameters could also include spectral or signal statistics.

According to the invention, these scan parameters can be adjusted or modified in near real time using the high speed feedback bus 112, 524. Through adjustments or modifications to these scan parameters certain processing operations or adaptations become available. Several examples are provided below for echo mode and flow mode.

In echo mode, the following adaptations are available. The ultrasound system could determine that a particular region of interest (ROI) should be rescanned at a different angle or frequency, and then using the high speed feedback bus 112, 524 adjust the scan parameters to effectuate the same. By adjusting the center frequency, the ultrasound system can optimize resolution and increase signal-to-noise ratio given an objective measure of noise level at a depth derived from signal statistics. An adjustment to the PRF can remove image artifacts such as reverberation. Adjustments to time gain control (TGC) curves for a look direction can be made to compensate for highly attenuated regions which produce acoustic "shadows" or less attenuated targets which produce bright regions distal to the target.

In flow mode, the following adaptations are available. The ultrasound system could use results from frequency and velocity estimates to adjust the PRF for subsequent scans, which increases the sensitivity of the velocity estimates by maximizing a parameter such as the amount of energy passing through a wall filter (WF). Ensemble length is the number of data points that pass to a flow estimator. In cases where strong echos, large vessels and/or high velocities are present, the ensemble length can be shortened for improved image frame rate. In cases where weak ethos, small vessels and/or low velocities are present, the ensemble length can be lengthened for better performance of color flow algorithms. This type of adjustment can be made dynamically throughout the processing of a single image or ensemble. The frame rate of a flow image is controlled by the number of firings which occur between subsequent firings in one look direction. A low PRF can be obtained in one look direction by firing interleaved lines in different look directions, thus maintaining a higher effective frame rate. Hence, by adjusting the interleave ratio and the PRF, the frame rate can be optimized for a particular flow condition. The focus can also be adapted to lie on or near regions of difficult flow to optimize the physical properties of the ultrasonic beam.

Although the back end processing subsystem described above utilizes substantially identical programmable processing elements, the back end processing subsystem could also include at least one special purpose board for performing specialized back end processing functions that can be implemented and carried out with greater efficiency on a specialized board. However, the thrust of the back end processing subsystem remains to be substantially identical programmable processing elements.

The bus structure between the processing elements or boards is largely parallel which allows varying number of processing elements or boards to be connected or unconnected without harming the functionality of the back end processing subsystem 104, 300, 500. Hence, if the back end processing subsystem 104, 300, 500 had, for example, three (3) boards initially, if the owner of the ultrasound system 102 desired to upgrade the ultrasound system 102 to provide greater speed performance or certain enhanced features that required additional processing power to be effectively performed, additional processing elements or boards could be inserted (plugged into) the back end processing subsystem 102, 300, 500 in a matter of minutes.

We claim:

1. An ultrasound imaging system, comprising:
    a transducer for sending acoustical signals towards a subject, the acoustical signals being formed in accordance with electrical scan signals;
    a front end subsystem, operatively connected to said transducer, for producing the electrical scan signals based on scan parameters, for receiving echo signals from the subject in response to the acoustical signals, and for producing vector signals from the echo signals;
    a back end processing subsystem for receiving the vector signals from said front end subsystem and processing the vector signals to produce image data and parameter information;
    a feedback link for feeding back the parameter information from said back end processing subsystem to said front end processing subsystem; and
    a display device for displaying an image in accordance with the image data.

2. An ultrasound imaging system as recited in claim 1, wherein the feedback of the parameter information is performed in near real-time by said feedback link.

3. An ultrasound imaging system as recited in claim 1, wherein the parameter information being fed back via said feedback link causes the scan parameters used by said front end subsystem to be modified to improve the image to be displayed.

4. An ultrasound imaging system as recited in claim 1, wherein after receiving a first group of the vector signals for the image, the first group of the vector signals is processed by said back end processing subsystem while at the same time a next group of the vector signals for the image is being received at said front end processing subsystem, and
    wherein the parameter information is updated as each group of the vector signals is being processed by said back end processing subsystem such that the scan parameters used by said front end processing subsystem to obtain subsequent groups of the echo signals are modified.

5. An ultrasound imaging system as recited in claim 4, wherein the modifications to the scan parameters operate to improve the image.

6. An ultrasound imaging system as recited in claim 1, wherein said back end processing subsystem comprises a plurality of substantially identical processing nodes.

7. An ultrasound imaging system as recited in claim 6, wherein the processing of said back end processing system has a computational load associated therewith, and wherein the computational load is distributed across said processing nodes.

8. An ultrasound imaging system as recited in claim 6, wherein the processing of said back end processing subsystem is allocated to said processing nodes based on predetermined criteria.

9. An ultrasound imaging system as recited in claim 6, wherein said processing nodes are circuit boards, and each of said circuit boards include a plurality of processors and a local board-level bus for interconnecting said processors.

10. An ultrasound imaging system as recited in claim 6, wherein performance of said back end processing subsystem degrades gradually with the failure of each of said processing nodes.

11. An ultrasound imaging system as recited in claim 6, wherein said ultrasound imaging system further comprises:
    a controller for controlling said ultrasound imaging system, the controlling including determining said processing nodes within said back end processing subsystem that have failed and then bypassing said processing nodes that have failed.

12. An ultrasound imaging system as recited in claim 11, wherein said controller operates to limit processing requirements of said back end processing subsystem when the number of said processing nodes that have failed exceeds a predetermined number.

13. An ultrasound imaging system as recited in claim 1, wherein said at least one link comprises a plurality of links.

14. An ultrasound imaging system as recited in claim 1, wherein said front end processing subsystem comprises:
    a transmitter for producing the electrical scan signals based on the scan parameters; and
    a receive beamformer for receiving echo signals from the subject.

15. An ultrasound imaging system as recited in claim 1, wherein said back end processing system comprises:
    a plurality of processing elements for performing processing tasks associated with the processing of the vector signals to produce the image data; and
    at least one link for carrying the parameter information from said processing elements to said feedback link.

16. An ultrasound imaging system as recited in claim 1, wherein said back end processing system comprises:
    a plurality of processing boards for performing processing tasks associated with the processing of the vector signals to produce the image data; and
    at least one board-level bus for communication with said feedback link, communication of control signals, and communication between processing boards.

17. An ultrasound imaging system, comprising:
a transducer for sending acoustical signals towards a subject, the acoustical signals being formed in accordance with electrical scan signals;
a front end subsystem, operatively connected to said transducer, for producing the electrical scan signals based on scan parameters, for receiving echo signals from the subject in response to the acoustical signals, and for producing vector signals from the echo signals;
a back end processing subsystem for receiving the vector signals from said front end subsystem and processing the vector signals to produce image data and parameter information, said back end processing subsystem includes at least a plurality of programmable processing nodes;
a controller for controlling said ultrasound imaging system, the controlling including determining said processing nodes within said back end processing subsystem that have failed and then bypassing said processing nodes that have failed; and
a display device for displaying an image in accordance with the image data.

18. An ultrasound imaging system as recited in claim 17, wherein said back end processing system comprises:
a plurality of processing elements for performing processing tasks associated with the processing of the vector signals to produce the image data; and
at least one link for carrying the parameter information from said processing elements to said front end subsystem.

19. An ultrasound imaging system as recited in claim 17, wherein said back end processing system comprises:
a plurality of processing boards for performing processing tasks associated with the processing of the vector signals to produce the image data; and
at least one board-level bus for communication to and from said front end subsystem, for communication of control signals and for communication between processing boards.

20. An ultrasound imaging system as recited in claim 19, wherein said processing boards include at least one processor, and
wherein said at least one board level bus includes at least
an input bus for supplying the vector signals from said front end processing subsystem;
an output bus for supplying the image data to said display device and for supplying the parameter information from said back end processing subsystem to said front end processing subsystem; and
an inter-board bus for transmitting data between said processing boards.

21. An ultrasound imaging system as recited in claim 20, wherein each of said processing boards comprise:
a plurality of processors; and
at least one processor level bus for transmitting data between said processors and for coupling with said at least one board level bus.

22. An ultrasound imaging system as recited in claim 17, wherein said controller operates to limit processing requirements of said back end processing subsystem when the number of said processing nodes that have failed exceeds a predetermined number.

23. An ultrasound imaging system, comprising:
a transducer for sending acoustical signals towards a subject, the acoustical signals being formed in accordance with electrical scan signals;
a front end subsystem, operatively connected to said transducer, for producing the electrical scan signals based on scan parameters, for receiving echo signals from the subject in response to the acoustical signals, and for producing vector signals from the echo signals;
a back end processing subsystem for receiving the vector signals from said front end subsystem and processing the vector signals to produce image data and parameter information, said back end processing subsystem includes at least a plurality of programmable processing nodes;
a controller for controlling said ultrasound imaging system, the controlling including determining a computational load associated with said back end processing subsystem and then distributing the computational load to said programmable processing nodes; and
a display device for displaying an image in accordance with the image data.

24. An ultrasound imaging system as recited in claim 23, wherein, before distributing the computational load to said programmable processing nodes, the controlling by said controller determines said programmable processing nodes that are faulty and then bypasses said faulty programmable processing nodes.

25. An ultrasound imaging system as recited in claim 23, wherein said back end processing system comprises:
a plurality of processing elements for performing processing tasks associated with the processing of the vector signals to produce the image data; and
at least one link for carrying the parameter information from said processing elements to said front end subsystem.

26. An ultrasound imaging system as recited in claim 23, wherein said back end processing system comprises:
a plurality of processing boards for performing processing tasks associated with the processing of the vector signals to produce the image data; and
at least one board-level bus for communication to and from said front end subsystem, for communication of control signals and for communication between processing boards.

27. An ultrasound imaging system as recited in claim 26, wherein said processing boards include at least one processor, and
wherein said at least one board level bus includes at least
an input bus for supplying the vector signals from said front end processing subsystem;
an output bus for supplying the image data to said display device and for supplying the parameter information from said back end processing subsystem to said front end processing subsystem; and
an inter-board bus for transmitting data between said processing boards.

28. An ultrasound imaging system as recited in claim 27, wherein each of said processing boards comprises:
a plurality of processors; and
at least one processor level bus for transmitting data between said processors and for coupling with said at least one board level bus.

29. A method for operating an ultrasound imaging system, said method comprising:
(a) sending acoustical signals towards a subject, the acoustical signals being formed in accordance with electrical scan signals;
(b) producing the electrical scan signals based on scan parameters and for receiving echo signals from the subject in response to the acoustical signals;

(c) producing vector signals from the echo signals;

(d) processing the vector signals to produce image data and parameter information;

(e) tuning the scan parameters in real time in accordance with the parameter information; and (f) displaying an image in accordance with the image data.

30. A method as recited in claim 29, wherein the ultrasound imaging system includes a plurality of processing nodes, wherein the image being produced is divided into a plurality of segments, and wherein said processing (d) simultaneously processes the vector signals associated with each of the segments of the image by processing each of the segments in a different one of the processing nodes.

31. A method for operating an ultrasound imaging system having a plurality of processing nodes for processing scan data, said method comprising:

(a) sending acoustical signals towards a subject, the acoustical signals being formed in accordance with electrical scan signals;

(b) producing the electrical scan signals based on scan parameters and for receiving echo signals from the subject in response to the acoustical signals;

(c) processing the echo signals into vector signals;

(d) determining a computational load for processing the vector signals;

(e) distributing the vector signals to the processing nodes for processing;

(f) processing the vector signals at the respective processing nodes to produce image data; and (g) displaying an image in accordance with the image data.

32. A method as recited in claim 31, wherein the processing nodes are substantially identical and programmable.

33. A method as recited in claim 31, wherein said distributing (e) comprises:

(e1) determining those of the processing nodes that are faulty;

(e2) bypassing the faulty processing nodes; and (e3) distributing the vector signals to the processing nodes other than the faulty processing nodes.

34. A method as recited in claim 33, wherein said processing (f) of the vector signals at the respective processing nodes produces parameter information in addition to the image data, and wherein said method further comprises (h) tuning the scan parameters in real time in accordance with the parameter information.

35. A method as recited in claim 34, wherein said tuning (h) occurs during said sending (a) and said producing (b) with respect to subsequent portions of the same image.

* * * * *